(12) United States Patent
Imhof

(10) Patent No.: US 11,480,536 B2
(45) Date of Patent: Oct. 25, 2022

(54) METHOD AND SENSOR FOR DETERMINING THE PERMITTIVITY OF A CELL POPULATION

(71) Applicant: HAMILTON BONADUZ AG, Bonaduz (CH)

(72) Inventor: Manuel Imhof, Felsberg (CH)

(73) Assignee: HAMILTON BONADUZ AG, Bonaduz (CH)

( * ) Notice: Subject to any disclaimer, the term of this patent is extended or adjusted under 35 U.S.C. 154(b) by 149 days.

(21) Appl. No.: 16/768,200

(22) PCT Filed: Nov. 29, 2018

(86) PCT No.: PCT/EP2018/083046
§ 371 (c)(1),
(2) Date: Aug. 14, 2020

(87) PCT Pub. No.: WO2019/106105
PCT Pub. Date: Jun. 6, 2019

(65) Prior Publication Data
US 2020/0386699 A1    Dec. 10, 2020

(30) Foreign Application Priority Data
Nov. 30, 2017   (DE) .......................... 102017128488.5

(51) Int. Cl.
*G01N 27/02*   (2006.01)
*G01N 15/08*   (2006.01)
*G01N 33/483*  (2006.01)

(52) U.S. Cl.
CPC ....... *G01N 27/026* (2013.01); *G01N 15/0806* (2013.01); *G01N 27/028* (2013.01); *G01N 33/4833* (2013.01)

(58) Field of Classification Search
CPC ............ G01N 15/0806; G01N 27/026; G01N 27/028; G01N 33/4833
See application file for complete search history.

(56) References Cited

U.S. PATENT DOCUMENTS 4,810,650 A * 3/1989 Kell ................. G01N 33/48735
                                                          435/287.1
5,569,591 A * 10/1996 Kell ................. G01N 33/48735
                                                          204/403.14
(Continued)

FOREIGN PATENT DOCUMENTS

FR    2867279 A1    9/2005
FR    2919724 A1    2/2009
(Continued)

*Primary Examiner* — Alesa Allgood
(74) *Attorney, Agent, or Firm* — Wiggin and Dana LLP; Thomas M. Landman

(57) ABSTRACT

A method for determining a value indicative of the permittivity of a cell population in the context of impedance spectroscopy comprises the following steps: generating an excitation current through the cell population, which oscillates with an excitation frequency; measuring a voltage in the cell population between a first measuring electrode (12) and a second measuring electrode (14); sampling the excitation current, wherein first sampled values for the excitation current are generated; sampling the voltage between the first measuring electrode (12) and the second measuring electrode (14), wherein second sampled values for the voltage between the first measuring electrode and the second measuring electrode are generated; and determining the value indicative of the permittivity of the cell population on the basis of the first sampled values and the second sampled values.

21 Claims, 4 Drawing Sheets

(56) References Cited

U.S. PATENT DOCUMENTS

| | | | |
|---|---|---|---|
| 5,602,333 A * | 2/1997 | Larrabee | G01F 23/26 |
| | | | 324/681 |
| 6,596,507 B2 | 7/2003 | Ossart | |
| 2003/0070942 A1 | 4/2003 | Ossart | |
| 2008/0054914 A1 | 3/2008 | Byington et al. | |
| 2008/0262748 A1 | 10/2008 | Ossart et al. | |
| 2008/0312843 A1 | 12/2008 | Esteban | |
| 2012/0007615 A1 | 1/2012 | Todd | |
| 2017/0071552 A1 | 3/2017 | Harpe et al. | |
| 2019/0079069 A1 | 3/2019 | Frank et al. | |

FOREIGN PATENT DOCUMENTS

| | | | | |
|---|---|---|---|---|
| FR | 2951547 A1 | | 4/2011 | |
| GB | 2447477 A | * | 9/2008 | G01R 27/2623 |
| GB | 2447477 A | | 9/2008 | |

* cited by examiner

METHOD AND SENSOR FOR DETERMINING THE PERMITTIVITY OF A CELL POPULATION

The present invention is in the field of impedance spectroscopy of cell populations. In particular, the present invention relates to determining the permittivity of a cell population or determining a value indicative of the permittivity of a cell population. The present invention further in particular relates to a method and a cell population sensor for determining a value indicative the permittivity of a cell population.

Electrical impedance spectroscopy methods are used as measurement methods for the nondestructive in-situ and in-vivo determination of frequency-dependent passive electrical properties of biological materials. Such a biological material can be, for example, a substance having a liquid and biological cells contained therein, which in its entirety will be referred to as cell population herein. The above-mentioned frequency-dependent passive electrical properties of the cell population can, inter alia, provide information about the number of living cells and/or the size of the cells and/or the homogeneity of the cells. Previous sensors and impedance spectroscopy methods are not always completely satisfactory with regard to the accuracy of the measurement results. The quality of the measurement results can also strongly fluctuate over a wide frequency range.

Accordingly, it would be desirable to provide a method and a cell population sensor for determining a value indicative of the permittivity of a cell population, which afford high measurement accuracy and permit reliable measurements in a wide frequency range.

Exemplary embodiments of the invention comprise a method for determining a value indicative of the permittivity of a cell population in the context of impedance spectroscopy, comprising the following steps: generating an excitation current through the cell population, which oscillates with an excitation frequency; measuring a voltage in the cell population between a first measuring electrode and a second measuring electrode; sampling the excitation current, wherein first sampled values for the excitation current are generated; sampling the voltage between the first measuring electrode and the second measuring electrode, wherein second sampled values for the voltage between the first measuring electrode and the second measuring electrode are generated; and determining the value indicative of the permittivity of the cell population on the basis of the first sampled values and the second sampled values.

Exemplary embodiments of the invention permit a highly accurate determination of a value indicative of the permittivity of a cell population over a wide frequency range. The sampling of the excitation current and the sampling of the voltage between the first measuring electrode and the second measuring electrode permit the generation of the first sampled values and the second sampled values at precisely defined points in time. These time-discretized sampled values can be analyzed and related after the sampling, without the signal processing, following the sampling, needing real-time capacities. A comparatively large database, clearly defined by the sampling in the time dimension, can be used, in order to determine the value indicative of the permittivity of the cell population with high accuracy. In comparison with previous approaches, which are based on determining characteristic properties of the cell population by means of complicated common analog signal processing of the excitation current and the voltage between the measuring electrodes, exemplary embodiments of the invention permit minimizing of the interferences after the sampling, since the signal processing of the discretized sampled values can be implemented in very robust manner. The interference effects between the measurement of excitation current and voltage between the measuring electrodes as well as the sampling of excitation current and voltage between the measuring electrodes can be kept very low, as compared to the interference effects along the analog signal processing chains of the earlier approaches. Additions, multiplications and integrations of analog signals for excitation current and voltage between the measuring electrodes, which are susceptible to interference and which were used in earlier approaches, can be eliminated. Furthermore, the sampling of the excitation current and the voltage between the first measuring electrode and the second measuring electrodes can be adapted to the excitation frequency, whereby high sampling accuracy at the relevant frequencies and spectral limitation of the interferences can be rendered possible.

The generation of the excitation current oscillating at the excitation frequency, the measurement of the voltage between the measuring electrodes, the sampling of the excitation current and the sampling of the voltage between the measuring electrodes take place simultaneously. In other words, the voltage between the first measuring electrode and the second measuring electrode is measured and sampled while the excitation current oscillating at the excitation frequency is applied to the cell population. Accordingly, the electrical behavior of the cell population is measured while the excitation current oscillating at the excitation frequency is applied.

The sampling of the excitation current and the sampling of the voltage between the first measuring electrode and the second measuring electrode can be a sampling of derived values of excitation current and voltage between the measuring electrodes. For example, a first signal can be generated for the excitation current, which represents the excitation current. This first signal can be a voltage signal, for example. The first signal can then be sampled directly or after amplification. Such signal processing, within the meaning of the present document, also falls under the terms of sampling the excitation current and generating first sampled values for the excitation current. Furthermore, it is possible that the voltage between the first measuring electrode and the second measuring electrode is tapped in the form of a second signal. This second signal can also be sampled either directly or after amplification. As with the sampling of the excitation current, such preprocessing of the second signal also falls under the terms of sampling the voltage between the first measuring electrode and the second measuring electrode and generating second sampled values in the meaning of the present document.

The cell population is an accumulation of biological cells. In particular, the cell population contains a significant proportion of living cells. The cells can be present in a carrier substance. For example, the cells can be taken up in the form of a suspension in a carrier liquid. The term cell population can refer to the accumulation of biological cells, including the carrier substance.

According to a further embodiment, the sampling of the excitation current and the sampling of the voltage between the first measuring electrode and the second measuring electrode each include converting an analog signal into a digital signal. In this way, time-discrete and value-discrete sampled values are provided both for the excitation current and for the voltage between the measuring electrodes. These can be further processed completely digitally and detached from real time, which results in great flexibility, accuracy and uniformity in further processing for the analysis of excitation current and voltage between the measuring electrodes. Highly accurate results can be achieved over a wide frequency range.

According to a further embodiment, the method further comprises the following steps: setting a first sampling rate for sampling the excitation current and setting a second sampling rate for sampling the voltage between the first measuring electrode and the second measuring electrode. In particular, setting of the first sampling rate and/or setting of the second sampling rate can be carried out on the basis of the excitation frequency of the excitation current. In this context, the first sampling rate and the second sampling rate can be identical or different. The setting of the first sampling rate and the setting of the second sampling rate permit the determination of the value indicative of the permittivity of the cell population to be adapted to the general conditions of a given measurement process, in particular to the excitation frequency of the excitation current for the given measurement process. In this way, it is possible to use optimized sampling rates for each measurement process, in particular to set a sampling rate that is optimized with regard to accuracy and/or signal processing complexity. The first sampling rate and the second sampling rate are used for sampling the excitation current and for sampling the voltage between the first measuring electrode and the second measuring electrode, respectively. Accordingly, the first sampling rate and the second sampling rate are set before the sampling of the excitation current and the voltage between the measuring electrodes.

According to a further embodiment, the first sampling rate and the second sampling rate are set to at least 4 times the excitation frequency of the excitation current. By using at least 4 times the excitation frequency of the excitation current for sampling excitation current and voltage between the measuring electrodes, it is ensured that excitation current and voltage between the measuring electrodes are sampled very accurately and that no signal information is lost around the excitation frequency. The sampling theorem is overfulfilled with a reassuring distance. In particular, the first sampling rate and the second sampling rate can be set to substantially 4 times the excitation frequency of the excitation current or even exactly to 4 times the excitation frequency of the excitation current.

According to a further embodiment, the excitation frequency of the excitation current is between 50 kHz and 20 MHz. An excitation current in this frequency range can be used to determine particularly relevant values which indicate the permittivity of the cell population and which, in particular, permit good conclusions as to the quantities and/or the size and/or homogeneity of the living cells of the biomass. The frequency range mentioned is in the so-called β-dispersion region of many cell populations, which will be discussed in detail below.

According to a further embodiment, sampling of the excitation current and sampling of the voltage between the first measuring electrode and the second measuring electrode takes places in synchronized manner. In this way, a highly precise correspondence between the sampled excitation current and the sampled voltage between the measuring electrodes can be achieved, whereby the phase shift between excitation current and voltage between the measuring electrodes can be determined with high accuracy, which in turn assists in providing a highly accurate determination of the value indicative of the permittivity of the cell population. Synchronized sampling of the excitation current and the voltage between the measuring electrodes is understood here to mean simultaneous sampling within the scope of manufacturing tolerances or sampling with an offset defined within the scope of manufacturing tolerances. The defined offset can be taken into account afterwards during further processing of the first and second sampled values.

According to a further embodiment, the fluctuation of the sampling time, i.e. the jitter, for sampling the excitation current and sampling the voltage between the first measuring electrode and the second measuring electrode is less than 500 fs. Such a design helps that the excitation current and the voltage between the measuring electrodes can be repeatedly sampled synchronously with high accuracy.

According to a further embodiment, the method comprises recording or writing the first sampled values and the second sampled values into a data memory. The provision of a data memory for the immediate recording of the first sampled values and the second sampled values creates a well-defined location at which the information about the excitation current and the voltage between the measuring electrodes is kept and from which further processing without real-time requirements and over a series of sampled values can take place. The data memory is a safe depot for the information obtained from excitation current and voltage between the measuring electrodes. In a further embodiment, the data memory is capable of recording/receiving data with a data acquisition rate of at least 1 Gbit/s. In this way, a complete recording of the sampled values can be ensured, even at a high sampling rate and high resolution.

According to a further embodiment, the step of determining the value indicative of the permittivity of the cell population comprises applying a complex Fourier transformation to the first sampled values and the second sampled values. In particular, a complex discrete Fourier transformation can be used. The sampled values of the excitation current and the sampled values of the voltage between the first measuring electrode and the second measuring electrode can be regarded as respective real parts of a complex current or voltage signal. The complex impedance between the excitation current and the voltage between the measuring electrodes can be determined by means of a complex Fourier transformation which takes the first and second sampled values jointly into account. In particular, the complex impedance at the excitation frequency can be determined, which can be the basis for the value indicative of the permittivity of the cell population.

According to a further embodiment, the step of determining the value indicative of the permittivity of the cell population comprises at least one of the following steps: determining the amplitude of the oscillating excitation current; determining that spectral component of the voltage that has the excitation frequency; and determining the phase shift between excitation current and said spectral component of the voltage. In particular, the step of determining the value indicative of the permittivity of the cell population can comprise exactly one or any subset or all of the steps mentioned.

According to a further embodiment, the step of determining the value indicative of the permittivity of the cell population comprises the following step: determining the value indicative of the permittivity of the cell population on the basis of one or more of the amplitude of the oscillating excitation current, the amplitude of that spectral component of the voltage that has the excitation frequency, and the phase shift between excitation current and said spectral component of the voltage. In particular, the amplitude of the oscillating excitation current and the amplitude of said spectral component of the voltage as well as the phase shift between excitation current and said spectral component of the voltage can be used to determine the value indicative of the permittivity of the cell population. In particular, the capacitance of the cell population between the measuring electrodes can be calculated on the basis of the amplitude of the oscillating excitation current, the amplitude of said spectral component of the voltage and the phase shift between excitation current and said spectral component of the voltage. The capacitance can be the value indicative of the permittivity of the cell population. It is also possible that the permittivity is determined from the capacitance or directly on the basis of the amplitude of the oscillating excitation current, the amplitude of said spectral component of the voltage and the phase shift between excitation current and said spectral component of the voltage.

According to a further embodiment, the value indicative of the permittivity of the cell population is a capacitance value, in particular a capacitance value that characterizes the capacitance of the cell population between the measuring electrodes, or a permittivity value, in particular the permittivity of the cell population itself.

According to a further embodiment, the step of sampling the excitation current comprises amplifying a first signal representing the excitation current, before the first sampled values are generated on the basis of the amplified first signal. In this way, the requirements for the accuracy of generating the first sampled values can be kept comparatively low. The amplification of the first signal allows small variations in the excitation current to be displayed on a larger scale. It can be advantageous for the overall complexity and/or accuracy of the overall system to invest in a highly linear amplification of the first signal and to have, on the other hand, lower requirements regarding the sampling of the amplified first signal.

According to a further embodiment, the step of sampling the voltage between the first measuring electrode and the second measuring electrode comprises amplifying a second signal representing the voltage between the first measuring electrode and the second measuring electrode, before the second sampled values are generated on the basis of the amplified second signal. The above considerations regarding overall complexity and/or overall accuracy apply analogously to the generation of the second sampled values from the voltage measured between the measuring electrodes.

According to a further embodiment, the method comprises the step of generating a first signal representing the excitation current via a measuring element. The measuring element can be a measuring resistor. In particular, the measuring resistor can have a resistance of $30\Omega$ to $50\Omega$. The first sampled values can be generated directly from the first signal obtained via the measuring element. However, it is also possible for the first signal to be amplified first, before the first sampled values are generated.

According to a further embodiment, the generation of the excitation current through the cell population, which oscillates with the excitation frequency, comprises a galvanic de-coupling between an alternating current source, outputting the excitation current, such as e.g. an oscillator, and the cell population. The capacitive artefacts in the cell population caused by the current source can be kept low, so that the galvanic de-coupling further assists the high measuring accuracy. It is also possible to reduce external interfering couplings in the region of the electrodes via the galvanic de-coupling. The galvanic de-coupling can be effected via a transformer, possibly in combination with a capacitor, as described in detail below.

According to a further embodiment, the method further comprises the following steps: determining a spectral power of the excitation current and that spectral component of the voltage that has the excitation frequency; determining the total power of excitation current and voltage between the first measuring electrode and the second measuring electrode; and determining a measure for the measurement accuracy of the value indicative of the permittivity of the cell population on the basis of said spectral power and the total power. In particular, the measure mentioned can be the signal-to-noise ratio between said spectral power and the noise power. The noise power can be calculated as the difference between the total power and the spectral power mentioned. By comparing the said spectral power and the total power, an estimate can be made as to what portion of the measured voltage between the measuring electrodes is due to the excitation current, i.e. what portion of the measured voltage represents the behavior of the cell population to be investigated. The noise power can include both reactions of the cell population and of the measuring apparatus at frequencies other than the excitation frequency, which are caused by the excitation current, as well as voltages otherwise generated in the cell population. Accordingly, the measure mentioned is an indicator of the degree to which the spectral component of the voltage, which has the excitation frequency, can be distorted. The measure can be output to a user as additional information. However, it can also be processed in such a way that the determination of the value indicative of the permittivity of the cell population is repeated either immediately or at a later time.

Exemplary embodiments of the invention further comprise a method for deriving at least one characteristic property of a cell population, comprising the following steps: performing the method for determining a value indicative of the permittivity of a cell population according to any of the above-described embodiments several times, wherein in performing said method several times, a plurality of different excitation frequencies are used and a plurality of values indicative of the permittivity of the cell population are determined for the plurality of different excitation frequencies; and deriving the at least one characteristic property of the cell population by relating the plurality of values indicative of the permittivity of the cell population. In this regard, said relating may include forming a difference between two values indicative of the permittivity of the cell population and/or determining the slope or gradient of a curve that is established by the plurality of values indicative of the permittivity of the cell population, and/or determining a turning point of a curve that is established by the plurality of values indicative of the permittivity of the cell population, and/or determining additional characteristic properties of the plurality of values indicative of the permittivity of the cell population. These characteristic properties of the set of values obtained allow conclusions to be drawn about the characteristic properties of the cell population. Due to the highly accurate determination of the plurality of values indicative of the permittivity of the cell population over a comparatively large frequency range, the characteristic properties of the cell population can also be determined with high accuracy.

According to a further embodiment, said method for determining a value indicative of the permittivity of a cell population is carried out for between 2 and 50 different excitation frequencies. In particular, the method for determining a value indicative of the permittivity of a cell population can be carried out for between 10 and 40 different excitation frequencies, further in particular for between 20 and 30 different excitation frequencies. It has been shown that, for the stated number of runs of the method and the corresponding number of values indicative of the permittivity of the cell population, in particular in the case of between 10 and 40 different excitation frequencies or further in particular in the case of between 20 and 30 different excitation frequencies, a good compromise between complexity of the method for deriving at least one characteristic property of the cell population and accuracy of the results with respect to the at least one characteristic property of the cell population can be achieved. In particular, especially meaningful curves of the value indicative of the permittivity of the cell population, in particular the permittivity itself, can be created for between 10 and 40 different excitation frequencies or further in particular for between 20 and 30 different excitation frequencies. The stated number of values allows for courses in relation to the excitation frequency to be created with sufficient accuracy in order to determine characteristic properties such as gradient and turning point with high accuracy.

According to a further embodiment, the different excitation frequencies are from a frequency range of 100 kHz to 10 MHz. The expression that the different excitation frequencies are from the frequency range mentioned means that at least the said frequency range is covered by the different excitation frequencies. This in turn means that the lowest excitation frequency is 100 kHz or less and that the highest excitation frequency is 10 MHz or more. In other words, the lowest excitation frequency and the highest excitation frequency form an excitation frequency range present therebetween, which includes at least the range between 100 kHz to 10 MHz. With the values indicative of the permittivity of the cell population for the excitation frequencies from 100 kHz to 10 MHz, one or more characteristic properties of a large number of cell populations can be determined with high accuracy.

In a further embodiment, the different excitation frequencies are from a frequency range of 50 kHz to 20 MHz. It has been shown that by sampling the excitation current and the voltage between the first measuring electrode and the second measuring electrode, as described above, highly accurate values indicative of the permittivity of the cell population can be determined also for such a large excitation frequency range between 50 kHz and 20 MHz. As a result, the derivation of the at least one characteristic property of the cell population can be refined even more. Thus, the above-described method for determining a value indicative of the permittivity of a cell population allows an expansion of the frequency range of the impedance spectroscopy and thus a more comprehensive determination of one or more characteristic properties of the cell population, without having to resort to additional and more complex methods. It is also possible that the method can be applied to an extended range of cell populations.

According to a further embodiment of the invention, each instance of said several times of performing the method for determining a value indicative of the permittivity of a cell population takes between 10 ms and 100 ms. In particular, each instance of said several times of performing the method takes between 30 ms and 70 ms. Accordingly, it is possible to derive one or more characteristic properties of a cell population in a very short period of time, in the order of a few seconds. As a result, the present method, according to exemplary embodiments of the invention, allows the user to determine one or more characteristic properties of the cell population almost immediately and therefore extremely conveniently. Taking samples from a cell population and time-shifted or off-site analysis of the samples can be dispensed with.

According to a further embodiment, deriving the at least one characteristic property of the cell population includes the creation of a course of the values indicative of the permittivity of the cell population over the different excitation frequencies. In other words, a curve can be drawn through the values indicative of the permittivity of the cell population against the excitation frequency. A so-called Cole-Cole fitting can be used in this regard. From the resulting curve or from the resulting course, characteristics such as e.g. differences between final values, gradients and turning points can be ascertained. The values indicative of the permittivity of the cell population can be directly the determined values, as described above, or calibrated versions of the determined values.

According to a further embodiment, the at least one characteristic property of the cell population comprises at least one property of the number of living cells, the size of the cells and the homogeneity of the cells.

Exemplary embodiments of the invention further comprise a cell population sensor for determining a value indicative of the permittivity of a cell population, comprising: an oscillator circuit; a first excitation electrode and a second excitation electrode which are coupled to the oscillator circuit, wherein an excitation current through the cell population, which oscillates with an excitation frequency, can be generated by means of the oscillator circuit via the first and the second excitation electrodes; a first measuring electrode and a second measuring electrode for measuring a voltage in the cell population between the first and second measuring electrodes; a first sampling circuit which is coupled to the first excitation electrode and/or the second excitation electrode and in operation provides first sampled values for the oscillating excitation current; a second sampling circuit which is coupled to the first and second measuring electrodes and in operation provides second sampled values for the voltage between the first and second measuring electrodes; and a data processing device which is coupled to the first sampling circuit and the second sampling circuit and which is configured to determine the value indicative of the permittivity of the cell population on the basis of the first sampled values and the second sampled values. The additional features, modifications and technical effects that have been described above with reference to the method for determining a value indicative of the permittivity of a cell population apply analogously to the cell population sensor.

The first and second sampling circuits operate simultaneously in operation, i.e. they generate the first sampled values for the excitation current and the second sampled values for the voltage between the first and the second measuring electrode in the same period of time. Furthermore, the first and second sampling circuits operate when the excitation current is applied to the cell population, i.e. the first and second sampling circuits operate in the same period of time as the oscillator circuit.

The term coupled is used herein to indicate that a signal or electric quantity can be transmitted from one entity to another, i.e. that there is some kind of connection between the entities. However, other components such as e.g. amplifiers, transformers or other electrical components, can be interposed.

The first sampling circuit can be coupled either to the first excitation electrode or to the second excitation electrode. It can also be coupled to both excitation electrodes. In general, the first sampling circuit can be coupled to one or both excitation electrodes in any suitable manner such that measurement of the excitation current is possible.

According to a further embodiment, the first sampling circuit is a first analog-to-digital converter and the second sampling circuit is a second analog-to-digital converter.

According to a further embodiment, the first sampling circuit has a first adjustable or settable sampling rate and the second sampling circuit has a second adjustable or settable sampling rate. According to a further embodiment, the first settable sampling rate and the second settable sampling rate can be set to at least 4 times the excitation frequency of the excitation current. This means that the first sampling circuit and the second sampling circuit are capable to sample the incoming signal with at least 4 times the excitation frequency. In a further embodiment, the first settable sampling rate and the second settable sampling rate can be set substantially to 4 times or exactly 4 times the excitation frequency of the excitation current.

According to a further embodiment, the oscillator circuit is configured to set the excitation frequency in a frequency range from 100 kHz to 10 MHz. This means that the oscillator circuit is capable to set the excitation frequency in a frequency range from 100 kHz to 10 MHz. This wording does not rule out that the oscillator circuit can set the excitation frequency beyond the specified frequency range. Rather, the wording means that the oscillator circuit is capable to set the excitation frequency at least in the frequency range from 100 kHz to 10 MHz. In particular, the oscillator circuit can be configured to set the excitation frequency at least in a frequency range from 50 kHz to 20 MHz.

According to a further embodiment, the first sampling circuit and the second sampling circuit are synchronized with regard to their sampling times.

According to a further embodiment, the fluctuation of the sampling time, i.e. the jitter, of the first sampling circuit and the second sampling circuit is less than 500 fs. Such a design helps that the excitation current and the voltage between the measuring electrodes can be repeatedly sampled synchronously with high accuracy.

According to a further embodiment, the first sampling circuit and the second sampling circuit are coupled to the data processing device via a data memory, the data memory in particular having a data acquisition rate of at least 1 Gbit/s. The data acquisition rate of at least 1 Gbit/s describes a possible data acquisition rate of at least 1 Gbit/s. The data does not have to be taken up by the data memory at this speed. Since the sampling frequency may be dependent on the excitation frequency, different data acquisition rates can result at the data memory during operation for different excitation frequencies.

According to a further embodiment, the data processing device is configured to determine the value indicative of the permittivity of the cell population from the first sampled values and the second sampled values by means of a complex Fourier transformation.

According to a further embodiment, the data processing device is configured to determine, from the first sampled values and the second sampled values, at least one of the amplitude of the oscillating excitation current, the amplitude of that spectral component of the voltage that has the excitation frequency, and the phase shift between excitation current and said spectral component of the voltage. In particular, the data processing device can be configured to determine exactly one or a subset or all of the values mentioned.

According to a further embodiment, the data processing device is configured to determine the value indicative of the permittivity of the cell population on the basis of one or more of the amplitude of the oscillating excitation current, the amplitude of that spectral component of the voltage that has the excitation frequency, and the phase shift between excitation current and said spectral component of the voltage. In particular, the data processing device can be configured to determine the value indicative of the permittivity of the cell population on the basis of the amplitude of the oscillating excitation current and the amplitude of said spectral component of the voltage and the phase shift between excitation current and said spectral component of the voltage.

According to a further embodiment, the value indicative of the permittivity of the cell population is a capacitance value or a permittivity value, in particular the permittivity of the cell population itself.

According to a further embodiment, the first sampling circuit is coupled to the first excitation electrode and/or the second excitation electrode via a first amplifier circuit and the second sampling circuit is coupled to the first and second measuring electrodes via a second amplifier circuit.

According to a further embodiment, a measuring element, in particular a measuring resistor, is coupled to the first excitation electrode or the second excitation electrode, and the first sampling circuit is configured to provide the first sampled values for the oscillating excitation current on the basis of the voltage drop at the measuring element. For reasons of symmetry, both excitation electrodes can be coupled to a respective measuring element, in particular a measuring resistor, although the first sampling circuit is coupled to one of the measuring elements only.

According to a further embodiment, the oscillator circuit is coupled to the first excitation electrode and the second excitation electrode via a transformer.

According to a further embodiment, the transformer has a parallel capacitance from 0.5 pF to 10 pF, in particular a parallel capacitance from 1 to 5 pF. The parallel capacitance can be a discrete component, such as a capacitor arranged in parallel to the transformer. However, it is also possible for the parallel capacitance to be a parasitic capacitance of the transformer, with the transformer being designed such that the parallel capacitance is within the specified value range. The term parallel capacitance denotes a coupling capacitance between the primary side and the secondary side of the transformer. With a parallel capacitance, the influence of interfering coupling capacitances, such as may exist between the electrodes and the wall of a container for the cell population or between the electrodes and other sensors provided, can be kept low. Since the smaller capacitance is often the determining factor in the case of the capacitance parallel to the transformer and other coupling capacities being present, the influence of an undesired interfering coupling capacitance can be reduced to the size of the parallel capacitance.

According to a further embodiment, the data processing device is configured to determine a spectral power of the excitation current and that spectral component of the voltage that has the excitation frequency and to determine the total power of excitation current and voltage between the first measuring electrode and the second measuring electrode. Furthermore, the data processing device can be configured to determine a measure for the measurement accuracy of the value indicative of the permittivity of the cell population on the basis of the said spectral power and the total power, said measure being in particular the signal-to-noise ratio on the basis of said spectral power and the total power.

According to a further embodiment, the conductors between the first sampling circuit and the first and/or second excitation electrode and the conductors between the second sampling circuit and the first and second measuring electrodes are substantially of equal length. The expression substantially of equal length means that the conductors between the second sampling circuit and the first and second measuring electrodes have between 90% and 110% of the length of the conductors between the first sampling circuit and the first and/or second excitation electrodes, in particular between 95% and 105%.

According to a further embodiment, the cell population sensor further comprises a control unit which is coupled to the oscillator circuit and in operation causes the oscillator circuit to successively generate excitation currents through the cell population which oscillate with different excitation frequencies. Furthermore, the control unit can be coupled to the first sampling circuit and the second sampling circuit and can be configured to transmit the currently generated excitation frequency to the first and second sampling circuits. The first and second sampling circuits can set the sampling rate in accordance therewith. The control unit can also be configured to transmit the currently generated excitation frequency to the data processing device.

Exemplary embodiments of the invention further comprise a computer program or a computer program product which contains program instructions which, when executed on a data processing system, perform a method according to any of the embodiments described above. In this context, the individual steps of the method can be initiated by the program instructions and executed by other components or executed in the data processing system itself.

Further exemplary embodiments of the invention will be described in the following with reference to the accompanying figures.

Figure 1:
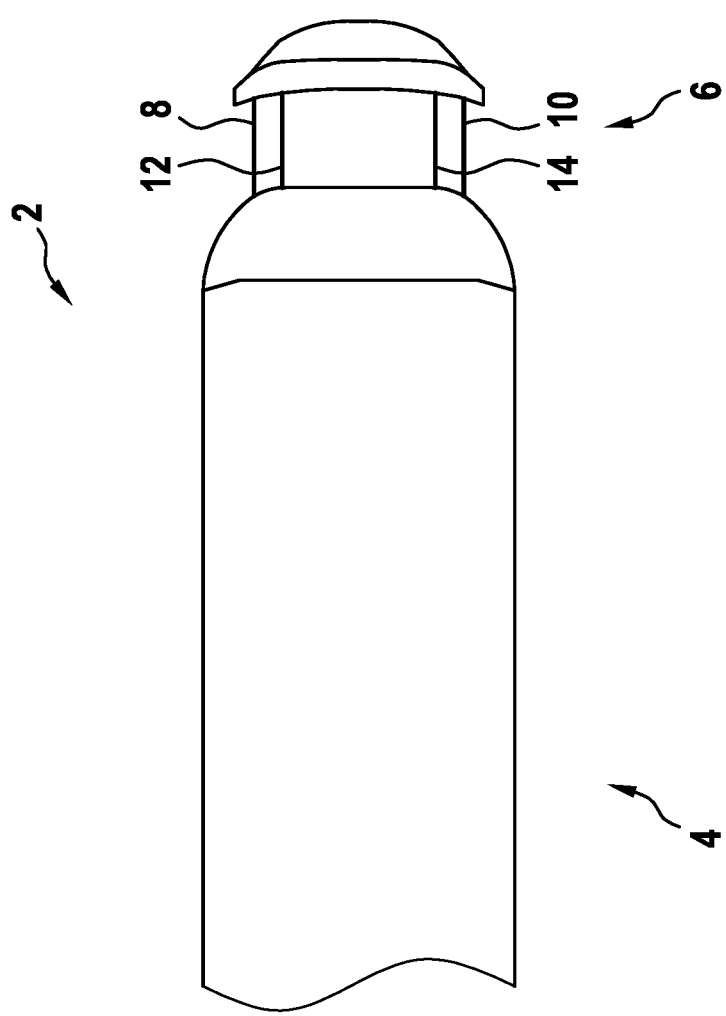
FIG. 1 shows a cell population sensor according to an exemplary embodiment of the invention in a side view.

FIG. 1 shows a cell population sensor 2 according to an exemplary embodiment of the invention in a side view. The cell population sensor 2 is designed to determine a value indicative of the permittivity of a cell population, as described below. The cell population sensor 2 is designed to be immersed into the cell population to be analyzed. For this purpose, the cell population sensor 2 has a stick-shaped sensor body 4, which is shown in a partial view in FIG. 1. The stick-shaped sensor body 4 may have a suitable length so that the analysis of the cell population can take place at a desired location in a container or reactor containing the cell population. A sensor head 6 is attached to the end of the sensor body 4.

The sensor head 6 has four electrodes. In particular, the sensor head 6 has a first excitation electrode 8, a second excitation electrode 10, a first measuring electrode 12 and a second measuring electrode 14. In the exemplary embodiment of FIG. 1, the four electrodes 8, 10, 12, 14 are elongated. They extend substantially parallel to the direction of extension of the sensor body 4. It is emphasized that the four electrodes can also be arranged in other geometric configurations, e.g. in the form of rings or ring sectors around the sensor head.

In the exemplary embodiment of FIG. 1, both the sensor body 4 and the part of the sensor head 6 that carries the electrodes are of cylindrical configuration. However, the sensor body 4 and the sensor head 6 may also have a different geometric basic structure.

In the exemplary embodiment of FIG. 1, the first excitation electrode 8 and the second excitation electrode 10 are arranged at diametrically opposite locations of the sensor head 6. The first measuring electrode 12 and the second measuring electrode 14 are arranged on one side of the sensor head 6, in the view of FIG. 1 on the side of the sensor head 6 facing the viewer, between the first excitation electrode 8 and the second excitation electrode 10.

The first measuring electrode 12 is arranged closer to the first excitation electrode 8 and the second measuring electrode 14 is arranged closer to the second excitation electrode 10. Furthermore, the first and second measuring electrodes 12, 14 are arranged comparatively close to the first and second excitation electrodes 8, 10. In particular, the first and second measuring electrodes 12, 14 are closer to the first and second excitation electrodes 8, 10 than to an imaginary center line between the first excitation electrode 8 and the second excitation electrode 10. By arranging the measuring electrodes 12, 14 between the excitation electrodes 8, 10 and in the vicinity of the excitation electrodes 8, 10, a comparatively high voltage can be measured upon application of the excitation current.

Figure 2:
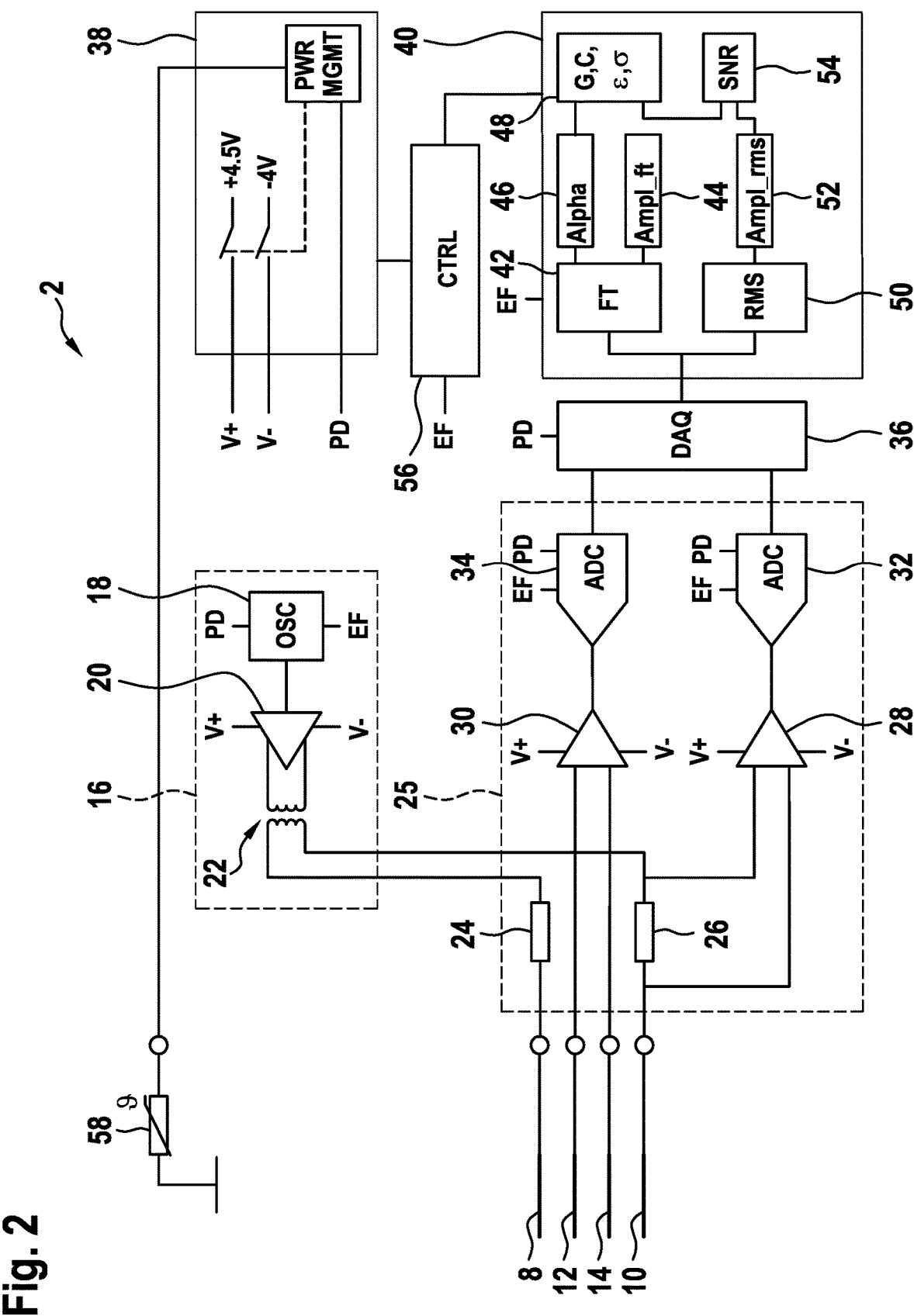
FIG. 2 shows a cell population sensor according to an exemplary embodiment of the invention, illustrated partially as a block diagram and partially as a circuit diagram.

FIG. 2 shows a cell population sensor 2 according to an exemplary embodiment of the invention, illustrated partly in a block diagram and partly in a circuit diagram. The components of the cell population sensor 2 of FIG. 2 can be present in a cell population sensor of the physical shape shown in FIG. 1. This means that the structure of the electrical components of the cell population sensor 2 of FIG. 1 can be embodied in accordance with the circuitry/signal processing structure of the cell population sensor 2 of FIG. 2. The components, shown to the right of the coupling points drawn as circles in FIG. 2, can be accommodated in the sensor body 4 or in a component adjoining the same.

The cell population sensor 2 comprises the above-described first excitation electrode 8, second excitation electrode 10, first measuring electrode 12 and second measuring electrode 14. The four electrodes 8, 10, 12, 14 are accessible from the outside, i.e. they are in contact with the cell population when the cell population sensor 2 is immersed in the cell population for analysis of the cell population. Furthermore, a temperature sensor 58 is provided, lying outside of the housing of the cell population sensor 2.

The cell population sensor 2 comprises an oscillator circuit 16, a signal detection and processing circuit 25, a data memory 36, a data processing device 40, a control unit 56 and a power management unit 38. The individual components and the functioning of these subsystems will be described in detail below.

The oscillator circuit 16 comprises an oscillator 18 which is coupled to an oscillation amplifier 20, which in turn is coupled to a transformer 22. The oscillator 18 is supplied with the desired excitation frequency EF via a control input. The excitation frequency EF is determined by the control unit 56, as described in detail below, and transferred to the oscillator 18. The oscillator 18 generates an oscillation with the excitation frequency EF, which is transferred to the oscillation amplifier 20. The oscillation amplifier 20 generates an excitation current having the excitation frequency EF through the primary winding of the transformer 22. The excitation current is transferred to the secondary winding of transformer 22 by induction, from where the current is applied to the first and second excitation electrodes 8, 10. One end of the secondary winding is connected to the first excitation electrode 8 via a first resistor 24 and the second end of the secondary winding is connected to the second excitation electrode 10 via a second resistor 26. Thus, there is formed a closed circuit from the first end of the secondary winding through the first resistor 24, via the first excitation electrode 8 through the cell population to the second excitation electrode 10, and through the second resistor 26 to the second end of the secondary winding. In this way, an excitation current through the cell population, which oscillates at the excitation frequency EF, is generated between the first excitation electrode and the second excitation electrode 10. In the exemplary embodiment of FIG. 2, the excitation current is a sinusoidal excitation current oscillating at the excitation frequency EF. Furthermore, the excitation current in the exemplary embodiment of FIG. 2 has an amplitude of 1 Vpp to 2 Vpp.

The transformer 22 provides for galvanic de-coupling or isolation between the oscillation amplifier 20 and the first and second excitation electrodes 8, 10. A coupling capacitance can be provided parallel to the transformer 22. It can then also be said that the transformer 22 has a parallel capacitance which is present between the primary winding and the secondary winding. The parallel capacitance can be a discrete component or a parasitic capacitance of the transformer. The parallel capacitance, by way of its arrangement in parallel to the transformer, can counteract interfering influences from other coupling capacitances, such as coupling capacitances between the electrodes and the container of the cell population and/or coupling capacitances between the electrodes and other sensors present in the cell population. The parallel capacitance can be between 1 pF and 5 pF.

The excitation current oscillating at the excitation frequency EF between the first excitation electrode 8 and the second excitation electrode 10 creates an alternating voltage between the first measuring electrode 12 and the second measuring electrode 14. Both the excitation current and the voltage between the measuring electrodes 12, 14 are detected and sampled by the signal detection and processing circuit 25. At the end of the signal processing in the signal detection and processing circuit 25 there are provided digital signals for the excitation current and the voltage between the measuring electrodes 12, 14.

A first signal, which represents the excitation current, is obtained in the following way. The second resistor 26 acts as a measuring resistor for the excitation current. The voltage across the measuring resistor 26 is tapped by means of two conductors and supplied as the first signal to a first amplifier circuit 28. The amplified first signal is fed to the first analog-to-digital converter 32. There the amplified first signal is converted into a digital signal, i.e. the amplified first signal is sampled and quantized. The resulting first sampled values are output to the data memory 36. It can be seen that the first resistor 24 is not required for the obtaining the first signal. For reasons of symmetry, however, the first resistor 24 is nevertheless provided. It can also be seen that tapping of a signal representing the excitation current can also take place at the first resistor 24. That is, the first amplifier circuit could also be coupled to the first excitation electrode 8 or the first resistor 24. The first resistor 24 and the second resistor 26 can each have a value of 30Ω to 50Ω.

The voltage between the first measuring electrode 12 and the second measuring electrode 14 forms a second signal, which is fed to a second amplifier circuit 30. The second signal is amplified there, and the amplified second signal is fed to a second analog-to-digital converter 34. The second analog-to-digital converter generates, analogously to the first analog-to-digital converter 32, second sampled values which are time-discrete and quantized. The second sampled values are also output to the data memory 36.

The first analog-to-digital converter 32 and the second analog-to-digital converter 34 also receive the information on the excitation frequency EF from the control unit 56. The first analog-to-digital converter 32 and the second analog-to-digital converter 34 use 4 times the excitation frequency EF for sampling the amplified first signal and the amplified second signal. Thus, the first analog-to-digital converter 32 and the second analog-to-digital converter 34 generate first and second sampled values for the excitation current and the voltage between the measuring electrodes 12, 14 at 4 times the excitation frequency EF.

The first and second sampled values output from the first analog-to-digital converter 32 and the second analog-to-digital converter 34 are buffered in the data memory 36. The data memory 36 thus represents a depot that records the first sampled values and the second sampled values and can make them available for further data processing independently of the real time. As a result, there are no longer any real-time requirements for the downstream components starting from the data memory 36. On the contrary, the downstream components can access a database accumulated in the data memory 36 over a certain period of time. The data memory 36 may be, for example, a DPRAM or any other suitable type of data memory.

The data memory 36 is coupled to the data processing device 40 and outputs the first sampled values for the excitation current and the second sampled values for the voltage between the first measuring electrode 12 and the second measuring electrode 14 to the data processing device 40. In the data processing device 40 there are two data processing paths which will be described below.

On the one hand, the first and second sampled values are transferred to a Fourier transformation module 42. The Fourier transformation module 42 performs a discrete, complex Fourier transformation with the first sampled values for the excitation current and the second sampled values for the voltage between the measuring electrodes 12, 14. The Fourier transformation performed in the Fourier transformation module 42 is discrete and complex, because the time-discrete sampled values for excitation current and voltage between the measuring electrodes are analyzed as mutually dependent variables. The result of this complex Fourier transformation are the amplitudes of the excitation current and the measured voltage for various frequencies as well as the phase shift a between excitation current and measured voltage for the various frequencies. In this context, it is possible that the Fourier transformation carries out a broad spectral analysis of the sampled values and that then all spectral components with the exception of the spectral components at the excitation frequency EF are rejected. However, it is also possible for the Fourier transformation to specifically determine the spectral component of the excitation current and the spectral component of the voltage between the first measuring electrode 12 and the second measuring electrode 14 at the excitation frequency. In this context, the Goertzel algorithm can also be used, with which the spectral components at the excitation frequency EF can be specifically determined.

The amplitude of the spectral component of the excitation current at the excitation frequency EF and the amplitude of the spectral component of the measured voltage at the excitation frequency EF are transferred via a first data transmission connection 44 to the permittivity determination module 48. The phase shift a between the spectral component of the excitation current at the excitation frequency and the spectral component of the measured voltage at the excitation frequency is transferred to the permittivity determination module 48 via a second data transmission connection 46.

The permittivity determination module 48 determines from the transferred parameters a conductance G, a capacitance C, the conductivity a of the cell population at the excitation frequency and the permittivity E of the cell population at the excitation frequency. The conductance G and the capacitance C can be calculated using the following two equations: $G=\cos(\alpha)*(i/u)$; $C=(\tan(\alpha)*G)/(2*\pi*f)$, where i and u denote the amplitude of the excitation current and the measured voltage of the spectral component at the excitation frequency. These formulas show that the capacitance can also be calculated from $\alpha$, i and u without going through the conductance. However, it is also possible for the conductance G and the capacitance C to be derived from more complex models and/or for the values, calculated using the above-mentioned equations, to be calibrated.

The conductivity $\sigma$ and the permittivity E are then calculated from the conductance G and the capacitance C using a model that represents the geometry of the cell population sensor and, if appropriate, additional factors of the measurement arrangement that influence the measurement results. In this way, the material properties conductivity $\sigma$ and permittivity E of the cell population are derived from the conductance G and the capacitance C. Approaches and methods known per se can be used to derive conductivity $\sigma$ and permittivity $\varepsilon$. Due to the highly precise acquisition of sampled values for the excitation current and for the voltage between the measuring electrodes, i.e. due to the high quality of the original data, as described herein, improved results as compared to previous cell population sensors can be achieved, even when using known methods for deriving conductivity $\sigma$ and permittivity $\varepsilon$.

On the other hand, the first and the second sampled values are transferred to an effective value calculation module 50. The effective value calculation module 50 determines the effective values of the excitation current and the voltage between the measuring electrodes 12, 14 via root mean square calculation. The effective values of the excitation current and the voltage are transferred to the SNR calculation module 54 via the third data transmission connection 52. The abbreviation SNR stands for signal-to-noise ratio. The SNR calculation module 54 also receives the amplitude of the spectral component of the excitation current at the excitation frequency EF and the amplitude of the spectral component of the measured voltage at the excitation frequency EF via the first data transmission connection 44.

The SNR calculation module 54 determines from the transferred data the spectral power of the excitation current and the voltage between the measuring electrodes 12, 14 at the excitation frequency and the total power of the excitation current and the voltage between the measuring electrodes 12, 14. The signal-to-noise ratio is determined on the basis of these two power quantities. The signal-to-noise ratio in particular can be determined as the ratio of the spectral power mentioned to the total power minus the spectral power mentioned. The signal-to-noise ratio can be regarded as a measure for the accuracy of the determination of the capacitance C or the permittivity $\varepsilon$. In particular, the signal-to-noise ratio can be regarded as a measure of the portion of the measured voltage that can be attributed to the response of the cell population to the excitation current, which is to be observed. It is emphasized that the said spectral power at the excitation frequency and the total power can also be related in other suitable ways in order to make a statement on the measurement accuracy. The signal-to-noise ratio is an exemplary measure.

The conductance G, the capacitance C, the conductivity $\sigma$, the permittivity $\varepsilon$ and the signal-to-noise ratio are thus available as results of the signal processing in the data processing device 40. In particular, these values are available as results for the excitation of the cell population with a specific excitation frequency. One or more of these values can be output for further processing. The output can take place to an external unit or, as shown in the exemplary embodiment of FIG. 2, to the control unit 56 present in the cell population sensor. In the exemplary embodiment in FIG. 2, the value determined for the permittivity $\varepsilon$ and the signal-to-noise ratio are output to the control unit 56.

The data processing device 40 can be implemented in software or can be present as an arrangement of hardware components. It is also possible for the data processing device 40 to be implemented partly in software and partly in hardware. The same applies to the control unit 56 described below.

The control unit 56 is connected to the power management unit 38, to the oscillator circuit 16, to the signal detection and processing circuit 25 and to the data processing device 40. The control unit 56 controls the method of determining a value indicative of the permittivity of a cell population in accordance with exemplary embodiments of the invention. For this purpose, the control unit 56 is configured to determine or set the excitation frequency EF for the method. In particular, the control unit is configured to determine a plurality of excitation frequencies for a plurality of runs of the method in the context of an impedance spectroscopy.

For a given run, the control unit 56 transmits the set excitation frequency EF to the oscillator circuit 16, where the oscillator 18 generates oscillation with the excitation frequency EF, to the signal detection and processing circuit 25, where the first analog-to-digital converter 32 and the second analog-to-digital converter 34 set the sampling rate on the basis of the excitation frequency EF, and to the data processing device 40, where the Fourier transformation module 42 analyzes the sampled values of excitation current and voltage between the measuring electrodes 12, 14 with respect to the spectral signal components at the excitation frequency.

Furthermore, in the exemplary embodiment of FIG. 2, the control unit 56 is coupled to the data processing device 40 in so far as the data processing device 40 transmits the permittivity $\varepsilon$ determined for the excitation frequency EF as well as the signal-to-noise ratio determined when determining the permittivity to the control unit 56. The control unit 56 is configured to decide on the basis of the determined signal-to-noise ratio whether a further run of the method is carried out in order to determine the permittivity for the given excitation frequency EF with a better signal-to-noise ratio or whether the result is accepted as having high quality. In the latter case, the control unit 56 can use impedance spectroscopy to set a new excitation frequency for the next run of the method. It is also possible for the control unit 56 to cause only one run of the method for each of the desired excitation frequencies, regardless of how good the signalto-noise ratio is, and to output the signal-to-noise ratio merely as additional information.

After a plurality of permittivity values have been determined for different excitation frequencies, the control unit 56 can derive one or more characteristic properties of the cell population from the plurality of permittivity values. For this purpose, the control unit can establish a curve through the plurality of permittivity values and derive the characteristic properties of the cell population from the curve, as described below with reference to FIG. 4. Such a correlation of the plurality of permittivity values can also take place outside the cell population sensor 2.

The control unit 56 is coupled to power management circuit 38 in order to signal the start and the end of a run of the method. On the basis of these signals, the power management circuit 38 supplies the oscillation amplifier 20 as well as the first amplifier circuit 28 and the second amplifier circuit 30 with the positive supply voltage V+ and the negative supply voltage V−, which in the present exemplary embodiment are +4.5 V and −4 V. After the end of a run of the method, the power management circuit 38 cuts off the positive and negative supply voltages and transmits a shutdown signal ("Power Down") to the oscillator 18, the first analog-to-digital converter 32, the second analog-to-digital converter 34 and the data memory 36. In this way, the cell population sensor saves electrical energy between the runs of the method for determining the permittivity.

The power management circuit 38 can obtain the electrical energy from outside of the cell population sensor 2 or via an internal energy reservoir, e.g. in the form of a battery.

For protection of the cell population sensor 2, the power management circuit 38 can open the voltage supply when the temperature sensor 58 measures a temperature above a predetermined threshold value.

Figure 3:
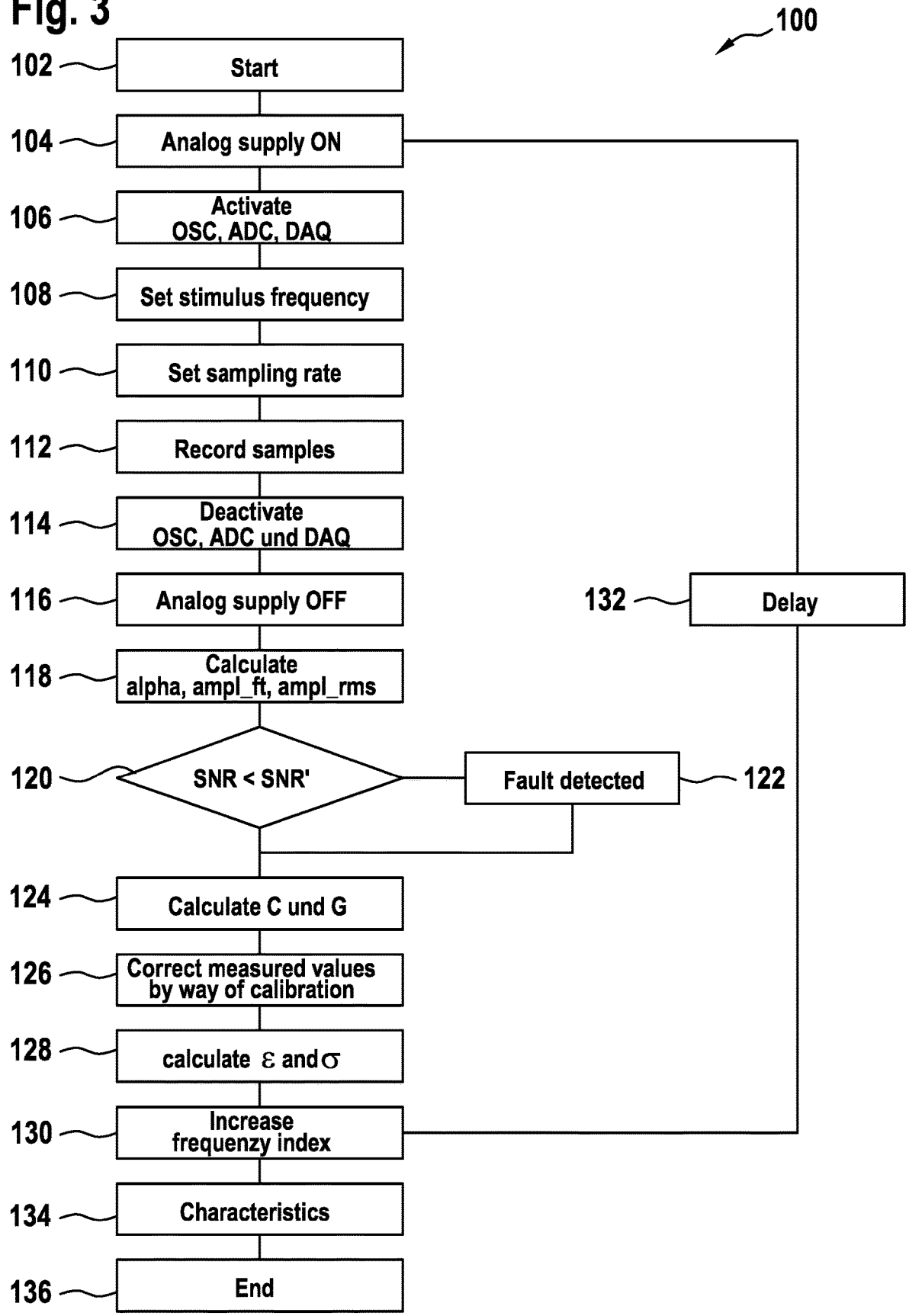
FIG. 3 shows a flow chart for a method for deriving at least one characteristic property of a cell population according to an exemplary embodiment of the invention.

FIG. 3 shows a method 100 for deriving at least one characteristic property of a cell population according to an exemplary embodiment of the invention. The method 100 can be carried out, for example, by the cell population sensor 2 shown in FIG. 1 and FIG. 2. For this purpose, the cell population sensor 2 is immersed in the cell population to be analyzed at least with its electrodes 8, 10, 12, 14.

The method 100 begins with the "start" step 102. In step 102, a frequency index n is set to 1. The frequency index indicates the instance of the run of the method for determining a value indicative of the permittivity of the cell population. In other words, the frequency index states the number of the excitation frequency that is used in the current run. Before starting the method, it is defined how many different excitation frequencies are used. For example, there may be used between 20 and 30 different excitation frequencies. There may also be a table that contains an excitation frequency for each value of the frequency index. It is also possible that the excitation frequency is determined in accordance with a predetermined rule for each value of the frequency index. For example, it is possible for the excitation frequencies to be selected in a regular manner from a logarithmic scale. For example, the following frequencies can be used as excitation frequencies: 50 kHz, 60 kHz, 70 kHz, 80 kHz, 90 kHz, 100 kHz, 200 kHz, 300 kHz, 400 kHz, 500 kHz, 600 kHz, 700 kHz, 800 kHz, 900 kHz, 1 MHz, 2 MHz, 3 MHz, 4 MHz, 5 MHz, 6 MHz, 7 MHz, 8 MHz, 9 MHz, 10 MHz, 20 MHz. However, any other suitable set of excitation frequencies is also possible for carrying out the method.

In step 104, the positive supply voltage V+ and the negative supply voltage V−, also referred to as analog supply, are switched on. In step 106, the oscillator 18, the first analog-to-digital converter 32, the second analog-to-digital converter 34 and the data memory 36 are activated. In step 108, the excitation frequency, also referred to as stimulus frequency, is set. For this purpose, the associated frequency is determined for the currently present value of the frequency index and set as the excitation frequency. The oscillation circuit 16 begins to apply the excitation current at the excitation frequency to the cell population. In step 110, the sampling rate in the first analog-to-digital converter 32 and the second analog-to-digital converter 34 is set to 4 times the excitation frequency. In step 112, first sampled values, also referred to as first samples, are generated in the first analog-to-digital converter 32. Furthermore, second sampled values, also referred to as second samples, are generated in the second analog-to-digital converter 34. The first sampled values and the second sampled values are recorded in the data memory 36 in step 112. In step 114, the oscillator 18, the first analog-to-digital converter 32, the second analog-to-digital converter 34 and the data memory 36 are deactivated. In step 118, the analog supply is switched off, i.e. the positive supply voltage V+ and the negative supply voltage V− are cut off.

In step 118, the amplitude of the excitation current, i.e. the amplitude of the excitation current oscillating at the excitation frequency, the amplitude of that spectral component of the measured voltage that has the excitation frequency, and the phase shift between the excitation current and the said spectral component of the measured voltage are determined. On the other hand, the effective values of the excitation current and the total voltage between the measuring electrodes 12, 14 are determined. In step 120, the signal-to-noise ratio SNR is determined on the basis of the spectral power at the excitation frequency and the total power and compared with a signal-to-noise ratio threshold value SNR'. In step 122, a fault is detected when the determined signal-to-noise ratio SNR falls below the threshold value SNR'.

In step 124, the conductance G and the capacitance C are calculated as described above. In step 126, the conductance G and/or the capacitance C are calibrated. It can also be said that the conductance G and/or the capacitance C are corrected using a calibration rule. The calibration data can be present in the form of a table and/or in functional form. The conductivity σ and the permittivity ε are calculated in step 128 on the basis of the calibrated values for the conductance G and the capacitance C.

In step 130, a decision is first made, on the basis of a fault possibly detected in step 122, as to whether the run for the present excitation frequency should be repeated. In this case, the frequency index is not increased and the method 100 continues with step 132. If no fault has been detected, it is checked in step 130 whether all the desired excitation frequencies have been used, i.e. whether the frequency index has reached its final value. If not, the frequency index is increased by 1 and method 100 continues with step 132. If the frequency index has reached its final value, the method 100 proceeds to step 134.

Step 132 merely means a delay before the method 100 is resumed at step 104. Due to the delay, the electrical effects in the cell population, which have been introduced in the previous run, can subside. The next run can start from a well-defined state of the cell population.

In step 134, one or more characteristics of the cell population are derived from the plurality of values for the permittivity of the cell population that have been determined for the different excitation frequencies. In particular, one or more of the number of living cells, the size of the cells and the homogeneity of the cells are derived, as described in detail below with reference to FIG. 4. The derived characteristics can be output to a user of the cell population sensor, for example via a screen. In addition to the characteristics, a quality measure can also be output, which can be derived from the SNR values discussed above for the individual runs for determining the permittivity values. The method 100 ends in step 136.

Figure 4:
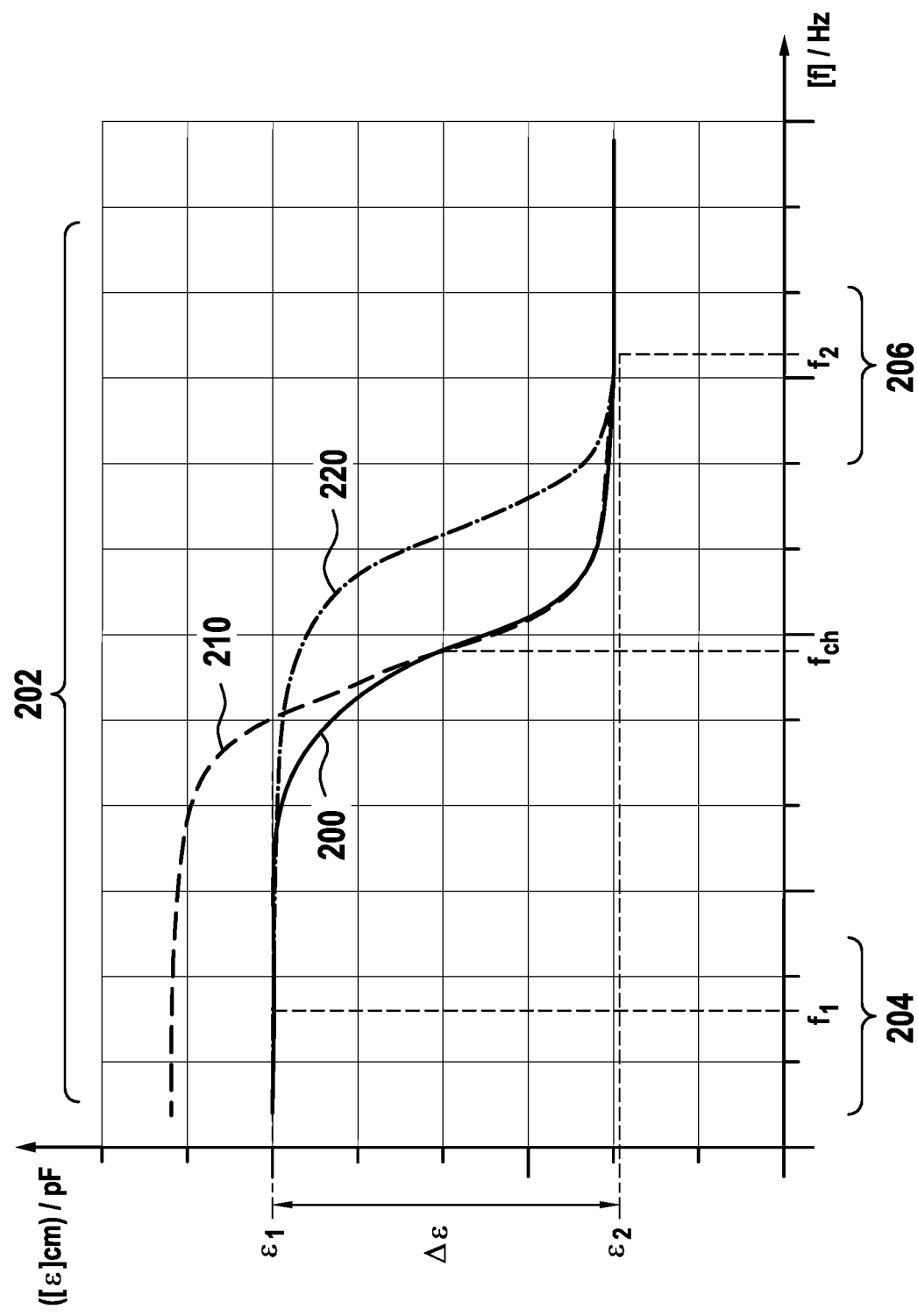
FIG. 4 shows an exemplary course of permittivity values in relation to the excitation frequency and illustrates deriving of characteristic properties of the cell population.

FIG. 4 shows purely qualitatively the course 200 of the permittivity ε of a cell population, plotted against the excitation frequency f. The course 200 is a purely exemplary curve which has been derived from a plurality of values for the permittivity, which have been determined by the method described above. For example, the course 200 may have been derived from the plurality of permittivity values using a Cole-Cole fitting.

Characteristics of the cell population can be derived from the course 200 as follows. FIG. 4 shows qualitatively that before a characteristic frequency $f_{ch}$ of the β dispersion region 202, there is a plateau region 204 in which the permittivity ε changes only slightly with frequency as compared to the region around the characteristic frequency $f_{ch}$, and that following the characteristic frequency $f_{ch}$, there is a further plateau region 206 which is different from the plateau region 22 before the characteristic frequency $f_{ch}$ and in which the permittivity ε, again compared to the region around the characteristic frequency $f_{ch}$, does not change strongly with frequency, either.

If one compares a permittivity value $ε_1$ representing the permittivity ε at an excitation frequency $f_1$ in the plateau region 204 with a permittivity value $ε_2$ at an excitation frequency $f_2$ in the plateau region 206, a differential value Δε of the two permittivity values can be determined from the permittivity values $ε_1$ and $ε_2$ determined at the excitation frequencies $f_1$ and $f_2$, respectively. The differential value Δε is a measure of the number of living cells contained in the cell population. The alternative permittivity curve 210 indicated with two dots and three lines would lead to a larger Δε at the respective excitation frequencies $f_1$ and $f_2$, which permits the conclusion that the cell population for which the permittivity curve 210 was obtained has more living cells in the same volume as the cell population on which the permittivity curve 200 is based.

A change in the characteristic frequency $f_{ch}$ indicates a change in the size of the cells or their physiology. A permittivity curve 220 with two dots and one line shows a higher characteristic frequency $f_{ch}$ in FIG. 4. The characteristic frequency $f_{ch}$ can be determined from the turning point of the course 200 between the plateau region 204 and the plateau region 206.

The slope or gradient of the permittivity curve at the point of its characteristic frequency $f_{ch}$ is a measure of the cell size distribution, with an increasing slope indicating a more heterogeneous cell size distribution and flattening courses of the permittivity curve 200 at the location of the characteristic frequency $f_{ch}$ indicating more homogeneous cell size distributions.

The permittivity curves shown in FIG. 4 can be in particular the courses of the real parts of the permittivity values determined.

In the exemplary embodiment of FIG. 4, $f_1$=50 kHz and $f_2$=20 MHz. Cell population sensors in accordance with exemplary embodiments of the invention permit high-precision determination of permittivity values over such a broad frequency range, as a result of which the β-dispersion region can be described very widely for many cell populations. In particular, the cell population sensor and the method for determining a value indicative of the permittivity of a cell population, according to exemplary embodiments of the invention, are suitable for cell populations with a conductivity of a few 0.1 mS/cm to 100 mS/cm and with a permittivity of a few pF/cm to a few hundred pF/cm.

An exemplary application for the cell population sensor and the method for determining a value indicative of the permittivity of a cell population according to exemplary embodiments of the invention are fermentation processes, for example when brewing beverages. However, the invention is generally broadly applicable for determining values indicative of the permittivity of a cell population.

Although the invention has been described with reference to exemplary embodiments, it will be apparent to those skilled in the art that various changes can be made and equivalents be used without departing from the scope of the invention. The invention is not intended to be limited by the specific embodiments described. Rather, it encompasses all the embodiments that are covered by the appended claims.

The invention claimed is:

1. A method for determining a value indicative of the permittivity of a cell population in the context of impedance spectroscopy, comprising the following steps:
   generating an excitation current through the cell population, which oscillates with an excitation frequency;
   measuring a voltage in the cell population between a first measuring electrode and a second measuring electrode;
   sampling the excitation current, wherein first sampled values for the excitation current are generated;
   sampling the voltage between the first measuring electrode and the second measuring electrode, wherein second sampled values for the voltage between the first measuring electrode and the second measuring electrode are generated, determining the value indicative of the permittivity of the cell population on the basis of the first sampled values and the second sampled values;
   determining a spectral power of the excitation current and that spectral component of the voltage that has the excitation frequency;
   determining the total power of excitation current and voltage between the first measuring electrode and the second measuring electrode; and
   determining a measure for the measurement accuracy of the value indicative of the permittivity of the cell population on the basis of said spectral power and the total power.

2. The method according to claim 1, further comprising the steps of:
   setting a first sampling rate for sampling the excitation current; and
   setting a second sampling rate for sampling the voltage between the first measuring electrode and the second measuring electrode,
   wherein the first sampling rate and the second sampling rate are set to at least 4 times the excitation frequency of the excitation current, in particular to substantially 4 times the excitation frequency of the excitation current.

3. The method according to claim 1, wherein the excitation frequency of the excitation current is between 50 kHz and 20 MHz.

4. The method according to claim 1, wherein the step of determining the value indicative of the permittivity of the cell population includes applying a complex Fourier transformation to the first sampled values and the second sampled values.

5. The method according to claim 1, wherein the step of determining the value indicative of the permittivity of the cell population comprises at least one of the following steps:

determining the amplitude of the oscillating excitation current;

determining that spectral component of the voltage that has the excitation frequency; and determining the phase shift between excitation current and said spectral component of the voltage.

6. The method according to claim 1, wherein generating the excitation current through the cell population, which oscillates with the excitation frequency, comprises a galvanic de-coupling between an alternating current source, outputting the excitation current, and the cell population.

7. The method according to claim 1,
wherein the measure for the measurement accuracy of the value indicative of the permittivity of the cell population is the signal-to-noise ratio on the basis of said spectral power and the total power.

8. A method for deriving at least one characteristic property of a cell population, comprising the following steps:
performing the method for determining a value indicative of the permittivity of a cell population according to claim 1 several times, using a plurality of different excitation frequencies, and determining a plurality of values indicative of the permittivity of the cell population for the plurality of different excitation frequencies; and deriving the at least one characteristic property of the cell population by relating the plurality of values indicative of the permittivity of the cell population.

9. The method according to claim 8, wherein said method for determining a value indicative of the permittivity of a cell population is carried out for between 2 and 50 different excitation frequencies, in particular for between 10 and 40 different excitation frequencies, more particularly for between 20 and 30 different excitation frequencies.

10. The method according to claim 8, wherein the different excitation frequencies are from a frequency range of 100 kHz to 10 MHz, in particular from a frequency range of 50 kHz to 20 MHz.

11. The method according to claim 8, wherein each instance of said several times of performing the method for determining a value indicative of the permittivity of a cell population takes between 10 ms and 100 ms, in particular between 30 ms and 70 ms.

12. The method according to claim 8, wherein the at least one characteristic property of the cell population comprises at least one property of the number of living cells, the size of the cells and the homogeneity of the cells.

13. A computer program which contains program instructions which, when executed on a data processing system, carry out a method according to claim 1.

14. A cell population sensor for determining a value indicative of the permittivity of a cell population, comprising:
an oscillator circuit;
a first excitation electrode and a second excitation electrode which are coupled to the oscillator circuit, wherein an excitation current through the cell population, which oscillates with an excitation frequency, can be generated by means of the oscillator circuit via the first and second excitation electrodes;
a first measuring electrode and a second measuring electrode for measuring a voltage in the cell population between the first and second measuring electrodes,
a first sampling circuit which is coupled to the first excitation electrode and/or the second excitation electrode and in operation provides first sampled values for the oscillating excitation current;

a second sampling circuit which is coupled to the first and second measuring electrodes and in operation provides second sampled values for the voltage between the first and second measuring electrodes; and a data processing device which is coupled to the first sampling circuit and the second sampling circuit and which is configured to determine the value indicative of the permittivity of the cell population on the basis of the first sampled values and the second sampled values,
wherein the data processing device is configured to determine a spectral power of the excitation current and that spectral component of the voltage that has the excitation frequency and to determine the total power of excitation current and voltage between the first measuring electrode and the second measuring electrode, and wherein the data processing device is further configured to determine a measure for the measuring accuracy of the value indicative of the permittivity of the cell population on the basis of the said spectral power and the total power.

15. The cell population sensor according to claim 14, wherein the first sampling circuit has a first settable sampling rate and wherein the second sampling circuit has a second settable sampling rate,
wherein the first settable sampling rate and the second settable sampling rate are settable to at least 4 times the excitation frequency of the excitation current, in particular substantially to 4 times the excitation frequency of the excitation current.

16. The cell population sensor according to claim 14, wherein the oscillator circuit is configured to set the excitation frequency in a frequency range from 100 kHz to 10 MHz, in particular in a frequency range from 50 kHz to 20 MHz.

17. The cell population sensor according to claim 14, wherein the data processing device is configured to determine, from the first sampled values and the second sampled values, at least one of the amplitude of the oscillating excitation current, the amplitude of that spectral component of the voltage that has the excitation frequency, and the phase shift between excitation current and said spectral component of the voltage, and
wherein the data processing device is configured to determine the value indicative of the permittivity of the cell population on the basis of one or more of the amplitude of the oscillating excitation current, the amplitude of that spectral component of the voltage that has the excitation frequency, and the phase shift between excitation current and said spectral component of the voltage.

18. The cell population sensor according to claim 14, wherein said measure for the measuring accuracy of the value indicative of the permittivity of the cell population is the signal-to-noise ratio on the basis of said spectral power and the total power.

19. The cell population sensor according to claim 14, wherein the oscillator circuit is coupled to the first excitation electrode and the second excitation electrode via a transformer.

20. The cell population sensor according to claim 19, wherein the transformer has a parallel capacitance from 0.5 to 10 pF, in particular from 1 to 5 pF.

21. A cell population sensor for determining a value indicative of the permittivity of a cell population, comprising:
an oscillator circuit;

a first excitation electrode and a second excitation electrode which are coupled to the oscillator circuit, wherein an excitation current through the cell population, which oscillates with an excitation frequency, can be generated by means of the oscillator circuit via the first and second excitation electrodes;

a first measuring electrode and a second measuring electrode for measuring a voltage in the cell population between the first and second measuring electrodes, a first sampling circuit which is coupled to the first excitation electrode and/or the second excitation electrode and in operation provides first sampled values for the oscillating excitation current;

a second sampling circuit which is coupled to the first and second measuring electrodes and in operation provides second sampled values for the voltage between the first and second measuring electrodes; and a data processing device which is coupled to the first sampling circuit and the second sampling circuit and which is configured to determine the value indicative of the permittivity of the cell population on the basis of the first sampled values and the second sampled values, wherein the oscillator circuit is coupled to the first excitation electrode and the second excitation electrode via a transformer, wherein the transformer has a parallel capacitance from 0.5 to 10 pF.

* * * * *